United States Patent [19]
Tomita et al.

[11] Patent Number: 5,304,251
[45] Date of Patent: Apr. 19, 1994

[54] CRYSTALLINE LACTULOSE TRIHYDRATE AND A METHOD FOR ITS MANUFACTURE

[75] Inventors: Mamoru Tomita; Seiichi Shimamura; Yoshitaka Tamura; Teruhiko Mizota; Satoshi Nakano; Itsuko Suzawa, all of Kanagawa, Japan

[73] Assignee: Morinaga Milk Industry Co., Ltd., Tokyo, Japan

[21] Appl. No.: 926,308

[22] Filed: Aug. 10, 1992

[30] Foreign Application Priority Data

Aug. 9, 1991 [JP] Japan ................................ 3-200928

[51] Int. Cl.$^5$ ...................... C13F 3/00; C07H 3/00; C08B 37/00
[52] U.S. Cl. ....................... 127/42; 127/29; 127/31; 426/658; 536/123.13
[58] Field of Search ............... 127/42, 29, 31; 426/658; 536/1.1

[56] References Cited

U.S. PATENT DOCUMENTS 4,999,058  3/1991  Kawashima et al. ............. 127/29
5,160,546  11/1992  Kawashima et al. ............. 127/30

Primary Examiner—Mark L. Bell
Assistant Examiner—Patricia L. Hailey
Attorney, Agent, or Firm—Wenderoth, Lind & Ponack

[57] ABSTRACT

A crystalline lactulose trihydrate having molecular formula of $C_{12}H_{22}O_{11}\cdot 3H_2O$ and a method for its manufacture, which comprises crystallization from a lactulose syrup at a temperature of 2°–20° C., the starting lactulose syrup having a lactulose content of 70–90% of a total solid matters by weight, and having been concentrated to the total solid matters of 65–75% by weight and a ratio of lactose to water of less than 10% by weight.

3 Claims, 1 Drawing Sheet

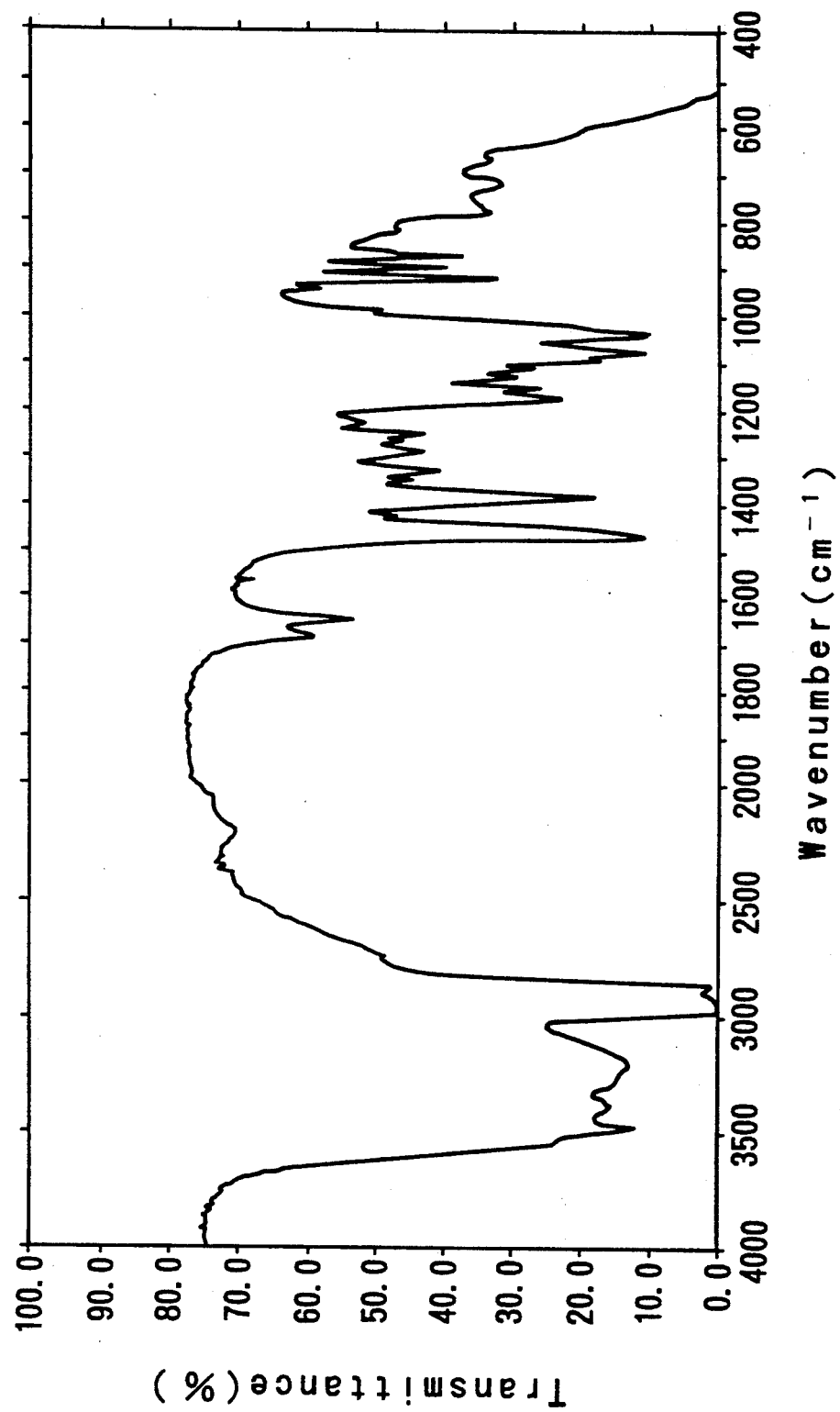

CRYSTALLINE LACTULOSE TRIHYDRATE AND A METHOD FOR ITS MANUFACTURE

FIELD OF THE INVENTION

This invention concerns crystalline lactulose trihydrate and a method for its manufacture. More precisely, the invention concerns a novel crystalline trihydrate of lactulose which has a promoting effect on the growth of Bifidobacterium.

The crystalline lactulose trihydrate of the invention is a substance having molecular formula of $C_{12}H_{22}O_{11}.3H_2O$ (referred to hereinafter as the trihydrate), and anhydrous lactulose is conventional anhydrous crystalline lactulose (referred to hereinafter as anhydrous material).

PRIOR ART

Lactulose (4-O-$\beta$-D-galactopyranosyl-D-fructofuranose) is a substance which is known as a growth factor for Bifidobacterium, and it is a disaccharide which does not exist in nature but which is produced by subjecting lactose to a Lobry de Bruyn transformation. As lactulose is highly soluble in water, it is difficult to obtain in the form of a stable powder and it is generally used in the form of a syrup. However, powdered or crystallized products have also been produced commercially using complicated processes.

Crystal precipitation methods using alcohols (methanol, ethanol etc) are known for obtaining lactulose crystals. Highly pure lactulose crystals can be obtained using these methods but reasonable quantities of these alcohols remain in the final product. There are also the problems in respect of the provision of highly pure lactulose in that the sugars other than the lactulose must be removed from the raw material syrup to increase the purity of the lactulose and in that complicated apparatus and procedures are required because of the use of alcohols.

Methods of obtaining crystals or powders of lactulose without using alcohols have also been developed [Japanese Patent Provisional Publication No. 200693/90 (referred to hereinafter as reference 1), Japanese Patent Provisional Publication No. 153692/89 (referred to hereinafter as reference 2) and Japanese Patent Provisional Publication No. 104800/86 (referred to hereinafter as reference 3)].

Reference 1 is a method of obtaining lactulose powder in which a lactulose syrup having been refined to a state of high purity is concentrated to a high concentration, a small amount of lactulose is seeded, crystals grow, the crystals obtained are dried under reduced pressure, and then the dry material is crushed.

Reference 2 is a method in which lactulose is crystallized and separated from an aqueous lactulose solution of which the lactulose concentration is 50–80% (by weight, the same applies hereinafter unless otherwise indicated), the lactose concentration is less than 5% of the lactulose concentration, the galactose concentration is less than 5% of the lactulose concentration and the concentration of other sugars is less than 4% of the lactulose concentration.

Reference 3 is a method in which an aqueous lactulose solution containing more than 60% lactulose in the solid matters is concentrated, the concentrate so obtained is maintained at 60°–110° C., seed crystals are added to the concentrate, the final solid matters of the concentrate is adjusted to 94–98%, it is frozen, and then the solid obtained is crushed.

However, in the conventional methods described above, in reference 1 the whole solid matters of the refined lactulose syrup is powdered and so it is impossible to raise the purity above that of the degree of refinement of the syrup.

Furthermore, in the case of reference 2 the lactulose concentration in the solid matters must be over 94.3% and the syrup of usual low lactulose purity must be refined to a very high degree of purity.

Moreover, the lactulose crystals which are obtained by means of these conventional methods are all anhydrous materials according to results of their analysis. If the anhydrous material is stored in an environment of high humidity it takes up water and solidifies, deliquescence arises and, in the case of prolonged storage, it turns brown and decomposes. Therefore, the product must be stored in full containers and special consideration must be given to the storage conditions.

As has been indicated above, in the conventional lactulose crystals were anhydrous lactulose, and stable lactulose crystals which have water of crystallization (hydrates) have not been disclosed in the literature and were unknown before application of the present invention.

SUMMARY OF THE INVENTION

It is an object of the invention to provide novel crystalline lactulose trihydrate having a high purity and a stability for prolonged periods of storage without containing organic solvents such as alcohol and without hygroscopicity. Another object of the invention is to provide a method for manufacturing novel crystalline lactulose trihydrate.

This invention provides a crystalline lactulose trihydrate having the molecular formula of $C_{12}H_{22}O_{11}.3H_2O$.

The invention also provides a method for the manufacture of crystalline lactulose trihydrate, comprising the steps of concentrating a lactulose syrup, which contains lactulose to the content of 70–90% by weight of the total solid matters, to ensure the total solid content up to 65–75% by weight and the ratio of lactose to water by weight less than 10%, cooling the concentrate to a temperature at 2° to 20° C., seeding the concentrate with lactulose crystals, forming a crystalline lactulose trihydrate by stirring, and separating the crystalline lactulose trihydrate.

BRIEF DESCRIPTION OF THE DRAWING

FIG. 1 represents infrared absorption spectrum of the crystalline lactulose trihydrate.

DETAILED DESCRIPTION OF THE INVENTION

As a result of research carried out in connection with stable crystals of lactulose, the inventors of this invention have discovered that a novel trihydrate of lactulose exists and that this novel trihydrate can be obtained easily from a syrup of the usual low lactulose purity, and it was confirmed that these crystals were very stable and useful, and the invention is based upon these discoveries.

A typical procedure to prepare the trihydrate of the invention is carried out in the following way.

The lactulose syrup which is used for a starting material may be material which has been manufactured using a known method (for example, Japanese Patent No. 874,954 etc.) or it may be commercial product. Usually, a lactulose syrup contains 45–55% lactulose, 2–8% galactose, 2–5% lactose and 2–8% of other sugars as well as water, and the lactulose purity in the solid matters is 70–90%. This conventional lactulose syrup can be used as it is without any purification for the starting material in the method of this invention. Moreover, in cases where the lactulose concentration in the solid matters is less than 70%, substances other than the lactulose are liable to crystallize and separation of the trihydrate become difficult which is undesirable.

The lactulose syrup contains lactose which has a low solubility and so it is desirable that the lactose crystals should be removed as far as possible in order to obtain the trihydrate. For this reason concentration is carried out until the ratio of lactose to water [lactose content/(lactose content+water content)] contained in the lactulose syrup is less than 10% and the total solid matters concentration is 65–75%. In cases where the total solid matters concentration is less than 65% the lactulose does not become super-saturated and so there is no precipitation of the trihydrate, or even if it is precipitated the recovery is low. Conversely, in cases where the total solid matters concentration exceeds 75% the viscosity of the lactulose syrup becomes high and it becomes difficult to handle. Next, the concentrated lactulose syrup is cooled to a temperature of 2°–20° C., lactulose seed crystals are added, the mixture is stirred and crystals are precipitated out. As low a temperature as possible is desirable for precipitating the crystals, and large crystals are precipitated out with gradual cooling and this is desirable. The lactulose for the seed crystal addition (seeding) is preferably in the form of the trihydrate.

After satisfactory crystals are formed, the trihydrate is separated using known methods (for example, centrifugal filtration, decantation etc.). The separated trihydrate is washed with water and the impurities are removed, but since the trihydrate has a high solubility this is preferably carried out with as small a quantity of cold water as possible.

The trihydrate washed with water is then dried. As the trihydrate melts, and join together and forms lumps when heated, it is difficult to dry. Hence, it is dried by fluid drying or vacuum drying, for example, at room temperature and the trihydrate is obtained.

The trihydrate obtained in the way outlined above has the physical and chemical properties indicated below and it also adsorbs heat when dissolved in water and so it feels cool when introduced into the mouth. Moreover, the trihydrate is stable over prolonged periods even in environments of high humidity.

The trihydrate of this invention has the following physical and chemical properties:

(1) Molecular Formula

It has the molecular formula of $C_{12}H_{22}O_{11} \cdot 3H_2O$.

(2) Elemental Analysis

The molar ratio of carbon:hydrogen:oxygen is 12:28:14.

(3) Molecular Weight

The molecular weight as determined by the cryoscopic method is 396 dalton.

(4) Water Content

The water content as determined by the Karl Fischer method is 13.6% by weight.

(5) Starting Point of Melting

The starting point of melting as determined by the capillary method is 58°–60° C.

(6) Specific Rotation

It exhibits mutarotation, but $-43.1° \pm 0.3°$ of specific rotation measured at 20° C. of a 1% by weight of aqueous solution in equilibrium state.

(7) Colour Reactions

Various color reactions were examined on the trihydrate dissolved in water. The results obtained are as follows.

| | |
|---|---|
| Fehling's test | Positive |
| Ammonia reaction* | Positive |
| Resolcinol-ferric salt-hydrochloric acid reaction | Positive |
| Ninhydrin reaction | Negative |

*Ammonia reaction was performed by the method described in the British Pharmacopeia (British Pharmacopeia, vol. 1, page 328, Office of the British Pharmacopeia Commission, 1988) as follows. Five ml of a 5% w/v solution was heated with 5 ml of 9M ammonia on a water-bath at 80° C. for 10 minutes.

(8) Qualitative and Quantitative Analysis of Lactulose

The analysises were performed by the method of the liquid chromatography (The United States Pharmacopeia, 22nd revision, Supplement 1, page 2138, United States Pharmacopeia Convention Inc., 1990) and the gas chromatography (Standards for Ingredients of Drugs not in the Japanese Pharmacopeia, page 1124, the Japanese Ministry of Welfare, 1986). All the results indicated the same column retention time as the anhydrous material and all analyses of lactulose content were 86.4%.

(9) Acidic, Basic or Neutral

Neutral.

(10) Infrared Absorption Spectrum

The infrared absorption spectrum of the crystalline lactulose trihydrate as measured by nujol mull method is as shown in FIG. 1. In FIG. 1, the abscissa and the ordinate are indicated the wave number and transmittance, respectively. The complicated absorption band at 3600–3200 cm$^{-1}$ ($\nu$OH) and 1200–1000 cm$^{-1}$ ($\nu$CO) are generally observed in the saccharides. The absorption bands of the crystalline lactulose trihydrate at 1200–900 cm$^{-1}$ differ from that of the anhydrous material.

(11) Solubility

Easily soluble in water. Soluble in methanol but the anhydride is precipitated rapidly. Insoluble in ethanol but rapidly forms the anhydrous material and dissolves. Insoluble in acetone, ethyl ether and benzene.

(12) Colour

Colourless or white.

The trihydrate of this invention has the same applications as the conventional anhydrous material and it can be used as it is or in admixture with other components in medicinal drugs such as constipation ameliorating drugs, drugs for the treatment of hepatic encephalopathy and drugs for the treatment of hepatic coma and for hyperammoniemia, in foodstuffs and medicinal drugs as a growth factor for Bifidobacterium and in foodstuff as a non-calorie sweetener, anti-tooth decay sweetener or low sweetness agent etc. In cases where the trihydrate of this invention is used in such applications it does not take up moisture and so the product quality does not deteriorate under the usual storage conditions and it exhibits better storage stability than the anhydrous material.

Experiments are indicated below and the invention is described in detail.

EXPERIMENT 1

This experiment was carried out in order to investigate the nature on dissolution in water.

Trihydrate which had been prepared using the same method as in Example 2 and the anhydrous material (melting point 167°–169° C.) obtained by recrystallizing this trihydrate twice from methanol (5 grams of each) were stored under an atmosphere maintained at 25.0° C. and then 50 ml of water which had been adjusted precisely to 25.0° C. was added and the mixtures were stirred and dissolved, and the temperature on complete dissolution was measured. The result was 23.3° C. for the trihydrate solution and 25.2° C. for the anhydrous material solution. The anhydrous material evolves a small amount of heat on dissolution whereas the trihydrate absorbs heat. The trihydrate is of a different nature from the anhydrous material. This results in a unique feature that is a feeling of sweetness accompanied by a feeling of cool when the trihydrate is introduced into the mouth.

EXPERIMENT 2

This experiment was carried out to investigate the stability under conditions of high humidity.

Samples of the same materials as in Experiment 1 (1 gram of each) were weighed out in weighing bottles and stored for 2–100 hours at 30° C. or 25° C. at a relative humidity of 100%, 93% or 81% and the rate of increase in weight (%) due to the uptake of water and the appearance was observed. The results obtained were as shown in Table 1.

It is clear from Table 1 that in comparison to the anhydrous material the trihydrate was stable even at high humidity and that while the anhydrous material took up moisture and gradually deliquesced at 30° C. and 25° C. with a relative humidity of 81%, the trihydrate took up only 1% of moisture and reached an equilibrium state, and a stable state was maintained.

TABLE 1

| Sample | Temp (°C.) | Storage Time (hr) | Rate of Increase in Weight due to the Uptake of Moisture (%) Relative Humidity (%) | | |
|---|---|---|---|---|---|
| | | | 100 | 93 | 81 |
| Trihydrate | 30 | 2 | 2.2 | 1.8 | 1.3 |
| | | 4 | 3.3 | 1.9 | 1.1 |
| | | 6 | 4.2 | 1.8 | 1.0 |
| | | 11 | 6.4 | 2.0 | 1.1 |
| | | 24 | 14.0* | 3.4 | 1.0 |
| | | 48 | 39.6**, | 11.9* | 1.2 |
| Trihydrate | 25 | 6 | 3.0 | 2.0 | 1.0 |
| | | 20 | 7.1 | 2.4 | 0.9 |
| | | 51 | 19.3* | 5.1 | 0.9 |
| | | 100 | 37.8** | 10.0* | 1.0 |
| Anhydrous material | 30 | 2 | 2.3 | 1.3 | 0.7 |
| | | 4 | 4.8 | 3.0 | 1.2 |
| | | 6 | 7.6 | 4.5 | 1.7 |
| | | 11 | 13.6* | 8.0 | 3.1 |
| | | 24 | 29.5** | 19.3** | 7.1 |
| | | 48 | 63.5*** | 46.3*** | 20.3** |
| Anhydrous material | 25 | 6 | 5.6 | 3.8 | 1.5 |
| | | 20 | 19.8* | 13.8* | 5.5 |
| | | 51 | 45.1*** | 31.4** | 12.5 |
| | | 100 | 66.1*** | 48.4*** | 22.9** |

(Notes)
*Exhibited some deliquescence.
**Most of the material was dissolved.
***The material was completely dissolved.

Hence, the trihydrate of this invention was seen to be much more stable at high humidity than the anhydrous material known in the past.

EFFECTS OF THE INVENTION

The following effects have been reported with this invention.

(1) The novel trihydrate of this invention is very stable in a high humidity environment.
(2) The novel trihydrate of this invention absorbs heat on dissolution in water and so it has a unique sweetness which is accompanied by a cool feeling.
(3) The method of this invention does not require refinement of the lactulose syrup and so the manufacturing process is very simple.
(4) The method of this invention does not involve the use of organic solvents and so a safe product is obtained.
(5) A highly pure trihydrate can be obtained by the method of this invention.

EXAMPLES

The following examples illustrate the present invention more specifically. These examples are not intended to limit the invention in any manner.

EXAMPLE 1

Commercial lactulose syrup (made by the Morinage Milk Industry Co., lactulose content 73.5%, lactose content 4.4%, galactose content 10.7% and other sugars 11.4% in solid matters) was concentrated to the ratio of lactose to water of 9.9% and a total solid matters of 71.5%, 10 kg of the concentrated liquid was cooled to 20° C., 30 grams of trihydrate seed crystals were added and the mixture was cooled gradually with stirring over a period of 7 days to 5° C. and crystals of the trihydrate were produced. After 10 days, the crystals were separated with a filter cloth type centrifugal separator (made by the Kokusan Centrifuge Co.) from the crystal containing liquid of which the solid matters content of the supernatant liquid had fallen to 68.9%, and the crystals were washed with cold water at 5° C. and about 1.4 kg of the trihydrate was obtained. This trihydrate was dried for 16 hours at 25° C. using a vacuum drier (made by the Yamato Kagaku Co.) and about 1.34 kg of a powder-like trihydrate was obtained.

The physical and chemical properties of the powder-like trihydrate obtained were as follows:

1) Water Content
    Water content by the Karl Fischer Method    13.7%

-continued

| | |
|---|---|
| Water content lost over diphosphorus pentoxide at room temperature | 0.1% |
| 2) Lactulose Assay Value | |
| Assay value by liquid chromatography in the same way as before | 84.9% |
| Calculated trihydrate in the material dried over diphosphorus pentoxide at room temperature | 98.4% |
| 3) Starting Point of Melting | |
| Value measured using the same method as before | 57–60° C. |
| 4) Specific Rotation | |
| Measured at 20° C. in a 1% aqueous solution of the material dried over diphosphorus pentoxide at room temperature | −43.0° C. |

EXAMPLE 2

Lactulose syrup (made by the Morinaga Milk Industry Co., lactulose content 85.6%, lactose content 3.1%, galactose content 5.2% and other sugars 6.1% in solid matters) was concentrated to the ratio of lactose to water of 6.9% and a total solid matters of 70.6%, 10 kg of the concentrated liquid was cooled to 15° C., 30 grams of trihydrate seed crystals were added and the mixture was cooled gradually with stirring over a period of 7 days to 5° C. and crystals of the trihydrate were produced. After 10 days, the crystals were separated with a filter cloth type centrifugal separator (made by the Kokusan Centrifuge Co.) from the crystal containing liquid of which the solid matters content of the supernatant liquid had fallen to 67.5%, and the crystals were washed with cold water at 5° C. and about 1.55 kg of the trihydrate was obtained. This trihydrate was dried for 4 hours at 30° C. using a fluid particle drier (made by the Okawara Seisakusho) and about 1.48 kg of a powder-like trihydrate was obtained.

The physical and chemical properties of the powder-like trihydrate obtained were as follows:

| | |
|---|---|
| 1) Water Content | |
| Water content by the Karl Fischer Method | 14.0% |
| Water content lost over diphosphorus pentoxide at room temperature | 0.4% |
| 2) Lactulose Assay Value | |
| Assay value by liquid chromatography in the same way as before | 85.8% |
| Calculated trihydrate in the material dried over diphosphorus pentoxide at room temperature | 99.7% |
| 3) Starting Point of Melting | |
| Value measured using the same method as before | 58–60° C. |
| 4) Specific Rotation | |
| Measured at 20° C. in a 1% aqueous solution of the material dried over diphosphorus pentoxide at room temperature | −42.8° |

EXAMPLE 3

Lactulose syrup (made by the Morinaga Milk Industry Co., lactulose content 88.5%, lactose content 3.0%, galactose content 3.7% and other sugars 4.8% in solid matters) was concentrated to the ratio of lactose to water of 5.6% and a total solid matters of 66.2%, 10 kg of the concentrated liquid was cooled to 15° C., 30 grams of trihydrate seed crystals were added and the mixture was cooled gradually with stirring over a period of 4 days to 2° C. and crystals of the trihydrate were produced. After 7 days, the crystals were separated with a filter cloth type centrifugal separator (made by the Kokusan Centrifuge Co.) from the crystal containing liquid of which the solid matters content of the supernatant liquid had fallen to 63.5%, and the crystals were washed with cold water at 5° C. and about 1.11 kg of the trihydrate was obtained. This trihydrate was dried for 4 hours at 25° C. using a fluid particle drier (made by the Okawara Seisakusho) and about 1.05 kg of a powder-like trihydrate was obtained.

The physical and chemical properties of the powder-like trihydrate obtained were as follows:

| | |
|---|---|
| 1) Water Content | |
| Water content by the Karl Fischer Method | 14.0% |
| Water content lost over diphosphorus pentoxide at room temperature | 0.5% |
| 2) Lactulose Assay Value | |
| Assay value by liquid chromatography in the same way as before | 85.5% |
| Calculated trihydrate in the material dried over diphosphorus pentoxide at room temperature | 99.8% |
| 3) Starting Point of Melting | |
| Value measured using the same method as before | 58–60° C. |
| 4) Specific Rotation | |
| Measured at 20° C. in a 1% aqueous solution of the material dried over diphosphorus pentoxide at room temperature | −42.9° |

What is claimed is:

1. A crystalline lactulose trihydrate having the molecular formula of $C_{12}H_{22}O_{11}\cdot 3H_2O$.

2. A crystalline lactulose trihydrate according to claim 1, wherein said crystalline lactulose trihydrate has the following physical and chemical properties:
    1) elementary analysis (in molar ratio): carbon: hydrogen: oxygen is 12:28:14;
    2) molecular weight: 396 dalton as determined by the cryoscopic method;
    3) moisture content: 13.6% by weight as determined by the Karl Fischer method;
    4) starting point of melting: 58°–60° C. as determined by the capillary method; and
    5) specific rotation: exhibiting mutarotation, but −43°±0.3° in specific rotation as measured at 20° C. of 1% by weight of aqueous solution in equilibrium state.

3. A method for the manufacture of crystalline lactulose trihydrate, comprising the steps of;
    concentrating a lactulose syrup, which contains lactulose to the content of 70–90% by weight of the total solid matters, to ensure the total solid content up to 65–75% by weight and the ratio of lactose to water by weight less than 10%,
    cooling the concentrate to a temperature at 2° to 20° C.,
    seeding the concentrate with lactulose crystals,
    forming a crystalline lactulose trihydrate by stirring, and
    separating the crystalline lactulose trihydrate.

* * * * *

REEXAMINATION CERTIFICATE (3248th)

United States Patent [19]
Tomita et al.

[11] B1 5,304,251
[45] Certificate Issued    Jul. 1, 1997

[54] CRYSTALLINE LACTULOSE TRIHYDRATE AND A METHOD FOR ITS MANUFACTURE

[75] Inventors: Mamoru Tomita; Seiichi Shimamura; Yoshitaka Tamura; Teruhiko Mizota; Satoshi Nakano; Itsuko Suzawa, all of Kanagawa, Japan

[73] Assignee: Morinaga Milk Industry Co., Ltd., Tokyo, Japan

Reexamination Request:
No. 90/004,172, Mar. 7, 1996

Reexamination Certificate for:
Patent No.: 5,304,251
Issued: Apr. 19, 1994
Appl. No.: 926,308
Filed: Aug. 10, 1992

[30] Foreign Application Priority Data

Aug. 9, 1991 [JP] Japan .................. 3-200928

[51] Int. Cl.⁶ .................. C13F 3/00; C07H 3/00; C08B 37/00
[52] U.S. Cl. .................. 127/42; 127/29; 127/31; 426/658; 536/123.13
[58] Field of Search .................. 127/29, 31, 42; 426/658; 536/123.13

[56] References Cited

U.S. PATENT DOCUMENTS

5,003,061  3/1991  Carobbi et al. .................. 536/127

FOREIGN PATENT DOCUMENTS

480519  4/1992  European Pat. Off. .......... C07H 3/04

OTHER PUBLICATIONS

Jeffrey, George A. "Crystal structure and n.m.r. analysis of lactulose trihydrate." Carbohydrate Research, 226 (1992), pp. 29–42. Mar. 1992.

Mizota, Teruhiko, et al. "Solubility of lactulose trihydrate." Carbohydrate Research 263 (1994), pp. 163–166. Dec. 1994.

*Primary Examiner*—Glenn Caldarola

[57] ABSTRACT

A crystalline lactulose trihydrate having molecular formula of $C_{12}H_{22}O_{11} \cdot 3H_2O$ and a method for its manufacture, which comprises crystallization from a lactulose syrup at a temperature of 2°–20° C., the starting lactulose syrup having a lactulose content of 70–90% of a total solid matters by weight, and having been concentrated to the total solid matters of 65–75% by weight and a ratio of lactose to water of less than 10% by weight.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 2 is cancelled.

Claims 1 and 3 are determined to be patentable as amended.

1. A crystalline lactulose trihydrate having the molecular formula of $C_{12}H_{22}O_{11}.3H_2O$, *wherein said crystalline lactulose trihydrate has the following physical and chemical properties:*

*1) elementary analysis (in molar ratio): carbon: hydrogen: oxygen is :12:28:14;*

*2) molecular weight: 396 dalton as determined by the cryoscopic method*

*3) moisture content: 13.6% by weight as determined by the Karl Fischer method;*

*4) starting point of melting: 58°–60° C. as determined by the capillary method; and*

*5) specific rotation: exhibiting mutarotation, but −43°±0.3° in specific rotation as measured at 20° C. in a 1% by weight aqueous solution in an equilibrium state.*

3. A method for the manufacture of *the* crystalline lactulose trihydrate *of claim 1*, comprising the steps of [:]*:* concentrating a lactulose syrup, which contains lactulose to the content of 70–90% by weight of the total solid matters, to ensure [the] *a* total solid content up to 65–75% by weight and [the] *a* ratio of lactose to water by weight *of* less than 10%, cooling the concentrate to a temperature at 2° to 20° C., seeding the concentrate with *a crystalline* lactulose [crystals, forming a] *trihydrate to form the* crystalline lactulose trihydrate *of claim 1* by stirring *for 4 to 7 days*, and separating the crystallline lactulose trihydrate *of claim 1.*

* * * * *